United States Patent [19]

Loev et al.

[11] Patent Number: 4,523,014

[45] Date of Patent: Jun. 11, 1985

[54] PIPERAZINES 1-HEXYL-4(3-KETOHEXYL)

[75] Inventors: Bernard Loev, Scarsdale; Ernest Magnien, Flushing, both of N.Y.

[73] Assignee: USV Pharmaceutical Corporation, Tuckahoe, N.Y.

[21] Appl. No.: 458,588

[22] Filed: Jan. 17, 1983

[51] Int. Cl.³ ............... C07D 241/04; A61K 31/495
[52] U.S. Cl. .................................. 544/386; 424/250; 544/399
[58] Field of Search ................. 544/386, 399; 424/250

[56] References Cited

U.S. PATENT DOCUMENTS 2,415,786 2/1947 Buck et al. .................. 544/386
3,373,163 3/1968 Loewe et al. ................ 544/386

FOREIGN PATENT DOCUMENTS 790800 2/1958 United Kingdom ............... 544/386

OTHER PUBLICATIONS

Lanyi, Chem. Abst., vol. 63, (1965), 5658d.
Lanyi, Chem. Abst., vol. 73, (1970), 23815r.

Primary Examiner—Donald G. Daus
Assistant Examiner—Cecilia Shen

[57] ABSTRACT

Substituted piperazines of the following formula

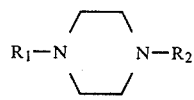

wherein $R_1$ is $C_3-C_7$ alkyl; $R_2$ is keto or hydroxy $C_3-C_7$ alkyl, keto $C_4-C_8$ cycloakyl, $C_4-C_8$ cycloalkyl keto $C_3-C_7$ alkyl and pharmaceutically acceptable acid addition salts thereof.

4 Claims, No Drawings

PIPERAZINES 1-HEXYL-4(3-KETOHEXYL)

This invention relates to new pharmaceutically-active compounds and more particularly, to certain new cyclic amines possessing useful pharmaceutical activities.

Pharmaceutically-active amines of the formula:

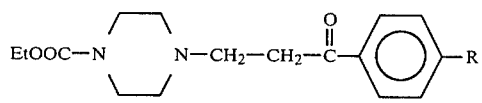

are reported to have analgesic, hypotensive and spasolytic activity (Lanyi, K. et al. Pharmazie, 1970 25 (3): 189). Other known cyclic amines are compounds of the formula:

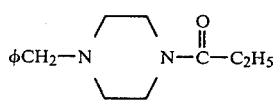

which is reported to be a slightly active analgesic [(Cignarella, G. et al. J. Med. Chem. II, 592, (1968)] and compounds of the formulas:

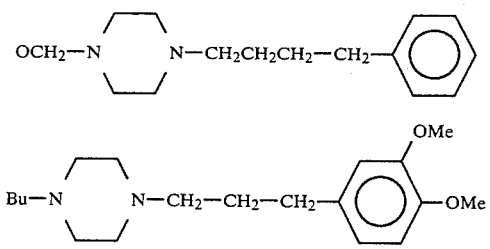

which have no reported pharmaceutical uses and have been described in Hungarian Patent Specification No. 152,051.

The new compounds of the present invention are cyclic amines of the following formula:

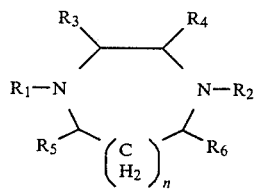

wherein
n=0 or 1;
$R_1$ is alkyl, cycloalkyl, alkenyl, alkynyl, aryl, aralkyl, carboalkoxy, formyl and ketoalkyl;
$R_2$ is ketoalkyl, hydroxyalkyl, carboxylakyl, alkanoyl, hydroxy, hydroxycycloalkyl, cycloalkyl, ketocycloalkyl, cycloalkylketoalkyl, alkylamido, carbalkoxy;
$R_3$, $R_4$, $R_5$, $R_6$ are each hydrogen, alkyl, aryl, aralkyl and cycloalkyl, and when taken together with the carbon stoms to which they are attached, $R_3$ and $R_4$ and/or $R_5$ and $R_6$ form a cyclic structure;
and acid addition salts thereof. The total number of carbon atoms in each such hydrocarbyl substituent representative of $R_1$ and $R_2$ can range up to about 10 carbon atoms, and may contain unsaturation, a heteroatom or other functionality as hereinbefore mentioned.

The substituted piperazines of the following general formula are preferred:

wherein, Z, $R_1$ and $R_2$ are as hereinbefore described, and $R_2$ preferably has a carbonyl function 2 or 3 carbon atoms removed from the piperazine nitrogen.

Most preferably, R is alkyl of 3-7 carbon atoms and $R_2$ is ketocycloalkyl (4–8Cs), cycloalkyl (4–8Cs), alkyl or a keto or hydroxyalkyl (3–7Cs) which may contain alkyl side chains, aryl is preferably phenyl or phenyl substituted with halo lower alkyl, lower alkoxy, hydroxy or trifluoromethyl.

The new compounds of this invention can be prepared by art-recognized procedures from known starting compounds. The following reaction sequence is exemplary using the preferred compounds:

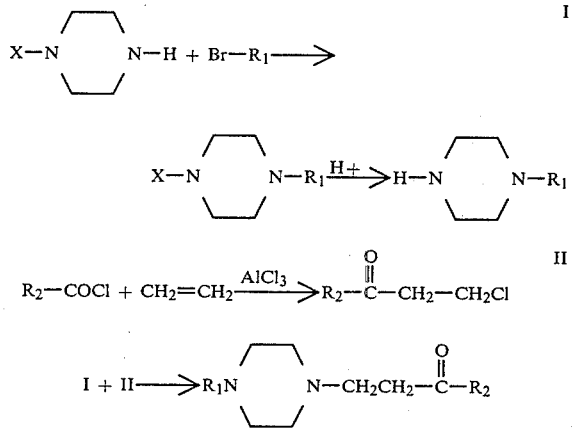

The substituent of the monosubstituted piperazine of formula I represents any of the substituent groups as hereinbefore enumerated to constitute $R_1$ and X being any suitable protecting group (e.g.,

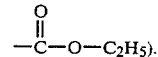

The ketoalkylchloride of formula II represents any of the precursor compounds which, upon reaction with a substituted piperazine of formula I, constitutes any of the functional groups hereinbefore described as representing $R_2$.

Methods for the preparation of the compounds of formula II include, in addition to the aluminum chloride catalyst reaction of an acid halide and an alkene of the foregoing illustration, the acid halide reaction with organocadmium compounds to form ketones, the aminoalkylation of a ketone to yield a desired amine (Mannich reaction), and the use of a Grignard reaction to produce an appropriate ketoalkylhalide.

The reaction of a formula I compound with a formula II compound may be effected by art recognized procedures. For instance, the mixture may be heated to effect a quicker, more efficient reaction, although heating is not essential to the process. The reaction mixture may then be partitioned between water and ether and the ether extract eventually dried over $MgSO_4$ and treated with ethanolic HCl to yield the product. Alternately, the reaction mixture can be filtered with the residue dissolved in water, basified, and extracted into toluene or other volatile organic solvent. The toluene can then be evaporated and the residues treated with a saturated solution of HCl in isopropanol. The salt can be filtered and crystallized from isopropanol.

Alternative methods of preparation of the object of this invention include, but are not limited to, dissolving the reaction mixture in isopropanol and acidfying with a solution of hydrochloric acid in isopropanol, and slurrying the reaction mixture with ether. Both of these methods may be followed by filtration and crystallization from acetonitrile to yield the product.

Using the procedures described, a wide variety of cyclic amines can be prepared, as are illustrated by the following:

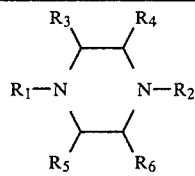

| $R_1$ | $R_2$ | $R_3$ | $R_4$ | $R_5$ | $R_6$ |
|---|---|---|---|---|---|
| —CH$_2$—C$_6$H$_5$ | —CH$_2$CH$_2$C(O)—C$_3$H$_7$ | H | H | H | H |
| —C(O)—OC$_2$H$_5$ | —CH$_2$CH$_2$C(O)—C$_3$H$_7$ | H | H | H | H |
| —CH$_2$CH$_2$C(O)—C$_3$H$_7$ | —CH$_2$CH$_2$C(O)—CH$_3$ | H | H | H | H |
| —C$_6$H$_{13}$ | —CH$_2$CH$_2$CH(OH)—C$_3$H$_7$ | H | H | H | H |
| —C$_6$H$_{13}$ | —CH$_2$CH$_2$C(O)—C$_3$H$_7$ | H | H | H | H |
| —C(O)—H | —CH$_2$CH$_2$C(O)—C$_2$H$_5$ | H | H | H | H |
| —C$_6$H$_{13}$ | —C(H)(CH$_3$)—C(O)—C$_3$H$_7$ | H | H | H | H |
| —C$_6$H$_{11}$ (cyclohexyl) | —CH$_2$C(O)—CH$_3$ | H | H | H | H |
| —CH$_2$—CH=CHCH$_2$CH$_3$ | —CH$_2$CH$_2$C(O)—C$_2$H$_5$ | H | H | H | H |
| —CH$_2$CH$_2$C≡CCH$_2$CH$_3$ | —CH$_2$CH$_2$C(O)—C$_4$H$_9$ | H | H | H | H |
| —C$_6$H$_{13}$ | 2-oxocyclohexyl | H | H | H | H |
| —C$_6$H$_5$ | —CH$_2$CH$_2$C(O)—C$_3$H$_7$ | H | H | H | H |
| —C(O)—O—C$_2$H$_5$ | —CH$_2$CH$_2$C(O)—C$_3$H$_7$ | H | H | H | H |

-continued

| R₁ | R₂ | R₃ | R₄ | R₅ | R₆ |
|---|---|---|---|---|---|
| —C₆H₁₃ | —CH₂CH₂C(=O)—C₃H₇ | —CH₂CH₂—C₆H₅ | H | H | H |
| —C₆H₁₃ | —CH₂CH₂C(OH)—C₂H₅ | H | cyclohexyl | H | H |
| —C₅H₁₁ | —CH₂—CH₂C(=O)—C₂H₅ | —(CH₂)₅— | | H | H |
| —C₆H₁₃ | —CH₂CH₂C(=O)—C₄H₉ | H | H | C₇H₅ | H |
| —C₆H₁₃ | —CH₂CH₂C(=O)—C₃H₇ | H | H | CH₂—CH₂—C₂H₅ | |
| —C₆H₁₃ | —CH₂—C(=O)—C₄H₉ | H | H | H | H |
| —C₆H₁₃ | —CH₂—CH₂CH₂—CH₂—C(=O)OH | H | H | H | H |
| —C₆H₁₃ | —OH | H | H | H | H |
| —C₆H₁₃ | cyclopentyl | —C₇H₁₅ | H | H | H |
| —C₆H₁₃ | —CH₂CH₂C(=O)—cyclobutyl | H | H | H | H |
| —C₆H₁₃ | —CH₂CH₂C(=O)—NH—C₂H₅ | H | C₂H₅ | H | H |
| —C₆H₁₃ | —C(=O)—O—C₃H₇ | H | H | —CH₂CH₂CH₂—C₆H₅ | H |
| —C₆H₁₃ | —CH₂CH₂C(=O)—C₂H₅ | H | H | H | —C₆H₅ |
| —C₆H₁₃ | —CH₂—CH(C₂H₅)—C(=O)—C₃H₇ | H | H | H | H |
| —C(=O)—C₅H₁₁ | CH₂—CH₂C(=O)—C₃H₇ | H | H | H | H |

The present new cyclic amines are therapeutically useful as such or can be employed in the form of salts in view of their basic nature. Thus, these compounds form salts with a wide variety of acids, inorganic and organic, including therapeutically-acceptable acids. The salts with therapeutically-acceptable acids are, of course, useful in the preparation of formulations where water solubility is desired. The salts with therapeutically-unacceptable acids are particularly useful in the isolation and purification of the present new compounds. Therefore, all acid salts of the present new compounds are contemplated by the present invention.

The pharmaceutically-acceptable acid addition salts are of particular value in therapy. These include salts of mineral acids such as hydrochloric, hydriodic, hydrobromic, phosphoric, metaphosphoric, nitric, sulfuric acids, as well as salts of organic acids such as tartaric, acetic, citric, malic, benzoic, glycolic, gluconic, succinic, arylsulfonic, e.g., p-toluenesulfonic acids, and the like. The pharmaceutically-unacceptable acid addition salts, while not useful for therapy, are valuable for isolation and purification of the new substances. Further, they are useful for the preparation of pharmaceutically-acceptable salts. Of this group, the more common salts include those formed with hydrofluoric and perchloric acids. Hydrofluoride salts are particularly useful for the preparation of the pharmaceutically-acceptable salts, e.g., the hydrochlorides, by solution in hydrochloric acid and crystallization of the hydrochloride salt formed. The perchloric acid salts are useful for purification and crystallization of the new products.

The compounds of the present invention have been shown to have potent pharmaceutical activity.

Some have shown cardiotonic activity, some have shown myocardial depressant activity, and still others have shown anti-allergic and bronchodilator activity.

For example, the following compounds are cardiotonic:
(A) 1-hexyl-4-(3-ketohexyl)piperazine dihydrochloride;
(B) 1-pentyl-4-(3-ketohexyl)piperazine dihydrochloride;
(C) 1-hexyl-4-(cyclohexyl-2-one)piperazine dihydrochloride.

For example, the following compounds have myocardiac depressant activity:
(A) 1-hexyl-4-(2-hydroxyhexyl)piperazine dihydrochloride;
(B) 1-heptyl-4-(3-ketohexyl)piperazine dihydrochloride.

The following compounds have anti-allergic and bronchodilator activities:
(A) 1-hexyl-4-(3-ketohexyl)homopiperazine dimaleate;
(B) 1-(3-cyclobutyl-3-ketopropyl)-4-hexylpiperazine dihydrochloride;
(C) 1-(2-ethyl-3-ketohexyl)-4-hexylpiperazine dihydrochloride;
(D) 1-hexyl-4-(3-keto-5-dimethylhexyl)piperazine dihydrochloride.

The therapeutic agents of this invention may be administered alone or in combination with pharmaceutically-acceptable carriers, the proportion of which is determined by the solubility and chemical nature of the compound, chosen route of administration and standard pharmaceutical practice. For example, they may be administered orally in the form of tablets or capsules containing such excipients as starch, milk sugar, certain types of clay and so forth. They may be administered orally in the form of solutions which may contain coloring and flavoring agents or they may be injected parenterally, that is, intramuscularly, intravenously or subcutaneously. For parenteral administration, they may be used in the form of a sterile solution containing other solutes, for example, enough saline or glucose to make the solution isotonic.

The physician will determine the dosage of the present therapeutic agents which will be most suitable and it will vary with the form of administration and the particular compound chosen, and furthermore, it will vary with the particular patient under treatment. He will generally wish to initiate treatment with small dosages substantially less than the optimum dose of the compound and increase the dosage by small increments until the optimum effect under the circumstances is reached. It will generally be found that when the composition is administered orally, larger quantities of the active agent will be required to produce the same effect as a smaller quantity given parenterally. The compounds are useful in the same manner as comparable therapeutic agents and the dosage level is of the same order of magnitude as is generally employed with these other therapeutic agents. The terapeutic dosage will generally be from 10 to 750 milligrams per day and higher although it may be administered in several different dosage units. Tablets containing from 10 to 250 mg. of active agent are particularly useful.

The following examples further illustrate the invention.

EXAMPLE I

1-Chloro-2-hexanone

A Grignard reagent was prepared from 1.5 moles of n-butylbromide and 1.5 moles of magnesium turnings in 600 ml of ether. To this mixture, 1.2 moles of chloroacetylchloride was added, over one hour. The reaction mixture was then refluxed for ten hours after which 200 ml of 6N hydrochloric acid was added over two hours. The ethereal layer was washed with water, 10% NaHCO$_3$, water, dried over Na$_2$SO$_4$, evaporated and distilled to obtain 45 g (33%) of product having a boiling point of 75°–79° C./13–14 mm.

1-Hexyl-4-(2-Ketohexyl)piperazine 2HCl

A solution of 8.5 g (0.07 mole) of 1-chloro-2-hexanone in 25 ml of ether was added dropwise to a mixture of 8.5 g (0.05 mole) of a n-hexyl piperazine and 10 g (0.1 mole) of triethylamine in 50 ml of ether. Addition was completed in 1 hour and the reaction mixture was stirred for 48 hours. The reaction mixture was filtered and the solvent was removed. The residue was dissolved in water, basified with 50% NaOH and extracted into toluene. The toluene was evaporated and the residue was treated with a saturated solution of HCl in isopropanol. The salt was filtered and crystallized twice from isopropanol to yield 6.2 g with a melting point of 190°–192° C.

EXAMPLE II

1-Chloro-3-hexanone

Ethylene gas was passed into a mixture of 250 g of anhydrous aluminum chloride in 700 ml of chloroform at −10° C. for 0.5 hours. Two hundred and fifty grams of n-butyrlchloride was added at once and ethylene was passed into the mixture for 3 hours at −10° C. The reaction mixture was poured over cracked ice, separated and washed with a saturated NaHCO$_3$ solution. The organic layer was evaporated and the residue distilled to give 137.8 g of material with a boiling point of 72°–78° C./30–34 mm.

1-Hexanoyl-4-(3-Ketohexyl)piperazine HCl

A mixture of 1.8 g (0.01 mole) of n-hexyl piperazine and 1.9 g (0.014 mole) of 1-chloro-3-hexanone was heated to 120° C. for 5 minutes. The reaction product was slurried with ether, filtered and crystallized from acetonitrile to yield 4.2 g of product having a melting point of 162°–164° C.

EXAMPLE III

1-Hexyl-4-(3-Ketohexyl)-Piperazine Dihydrochloride

A mixture of 15.3 g (0.09 mole) of n-hexyl piperazine and 12.3 g (0.091 mole) of 1-chloro-3-hexanone was heated to 100° C. for 5 minutes, cooled and dissolved in isopropanol. Isopropanolic HCl was added until acidic. Ether was added and the salt was filtered off. The product was crystallized from acetonitrile to yield 16.5 g of product with a melting point of 225°–230° C.

EXAMPLE IV

1-Hexyl-4-(3-Ketophenyl)-piperazine Dihydrochloride

A mixture of 8.5 g (0.05 mole) of a n-hexyl piperazine and 6.8 g (0.056 mole) of 1-chloro-3-pentanone was heated to 140° for 5 minutes. The reaction product was dissolved in isopropanol and acidified with a solution of HCl in isopropanol. The dihydrochloride salt was filtered and crystallized from acetonitrile to give 11.0 g of white solid with a melting point of 230°–233° C.

EXAMPLE V

1-Hexyl-4-(2-Ethyl-3-Ketohexyl)Piperazine Dihydrochloride

A mixture of 4.6 g (0.027 mole) of 1-hexyl piperazine and 3.7 g (0.0294 mole) of 2-methylene-4-heptanone was heated at 120° C. for 2 hours and for 3 hours at 100° C. The mixture was cooled and partitioned between water and ether. The ether layer was washed twice with water and then extracted with 1N HCl. The aqueous extract was basified with 50% NaOH and extracted with ether. The ether extract was dried over $MgSO_4$ and treated with ethanolic HCl to give 7.6 g of product which was crystallized from acetonitrile to yield 5.4 g of product with a melting point of 198°–201° C.

While there have been described what are presently believed to be preferred embodiments of the invention, it will be apparent to a person skilled in the art that numerous changes can be made in the ingredients, conditions and proportions set forth in the foregoing embodiments without departing from the invention as described herein and as defined in the appended claims.

What is claimed is:
1. 1-Hexyl-4-(3-ketohexyl)piperazine.
2. 1-Hexyl-4-(2-ethyl-3-ketohexyl)piperazine.
3. A hydrocloride salt of the compound of claim 1.
4. A hydrochloride salt of the compound of claim 2.

* * * * *